United States Patent [19]

Cartmell et al.

[11] Patent Number: 5,480,377

[45] Date of Patent: * Jan. 2, 1996

[54] WOUND DRESSING HAVING A ROLL CONFIGURATION

[75] Inventors: James V. Cartmell, Xenia; Wayne R. Sturtevant, Centerville; Michael L. Wolf, West Milton; Michael J. Allaire, Cincinnati, all of Ohio

[73] Assignee: New Dimensions in Medicine, Inc., Dayton, Ohio

[*] Notice: The portion of the term of this patent subsequent to May 26, 2009, has been disclaimed.

[21] Appl. No.: 202,509

[22] Filed: Feb. 28, 1994

Related U.S. Application Data

[63] Continuation of Ser. No. 741,318, Aug. 17, 1991, abandoned.

[51] Int. Cl.⁶ .......................... A61F 13/00; A61F 15/00; A61L 15/00
[52] U.S. Cl. .......................... 602/48; 602/58; 602/42; 604/372
[58] Field of Search .................. 602/41, 42, 48, 602/49, 50, 51, 54, 56, 58; 604/369, 372

[56] References Cited

U.S. PATENT DOCUMENTS

| | | | |
|---|---|---|---|
| 3,214,501 | 10/1965 | Strauss | 264/49 |
| 3,249,109 | 5/1966 | Maeth et al. | 128/268 |
| 4,226,232 | 10/1980 | Spence | 128/156 |
| 4,377,160 | 3/1983 | Romaine | 128/156 |
| 4,393,048 | 7/1983 | Mason, Jr. et al. | 424/132 |
| 4,657,006 | 4/1987 | Rawlings et al. | 128/156 |
| 4,661,099 | 4/1987 | von Bittera et al. | 604/290 |
| 4,668,564 | 5/1987 | Orchard | 428/246 |
| 4,743,499 | 5/1988 | Volke | 428/317.3 |
| 4,770,299 | 9/1988 | Parker | 206/409 |
| 4,867,821 | 9/1989 | Morgan | 156/152 |
| 4,899,738 | 2/1990 | Parker | 128/90 |
| 4,909,244 | 3/1990 | Quarfoot et al. | 128/156 |
| 4,911,155 | 3/1990 | Delanney | 128/155 |
| 5,003,970 | 4/1991 | Parker et al. | 128/90 |
| 5,006,401 | 4/1991 | Frank | 428/231 |
| 5,025,783 | 6/1991 | Lamb | 128/156 |
| 5,059,424 | 10/1991 | Cartmell et al. | 424/443 |
| 5,106,629 | 4/1992 | Cartmell et al. | 424/445 |
| 5,115,801 | 5/1992 | Cartmell et al. | 602/48 |

FOREIGN PATENT DOCUMENTS

| | | |
|---|---|---|
| 19489 | 8/1990 | Australia . |
| 0190814 | 8/1986 | European Pat. Off. . |
| 50513 | 11/1980 | Ireland . |

*Primary Examiner*—Paul B. Prebilic
*Attorney, Agent, or Firm*—Killworth, Gottman, Hagan & Schaeff

[57] ABSTRACT

A wound dressing product is provided which includes a wound dressing laminate having a plurality of layers including a backing layer which forms a first side of the wound dressing laminate and a hydrogel layer which forms a second side of the wound dressing laminate. The wound dressing laminate is spirally wrapped about a center axis such that the wound dressing laminate terminates at a leading end and the first side of the wound dressing laminate forms the outer surface of the wound dressing product.

12 Claims, 2 Drawing Sheets

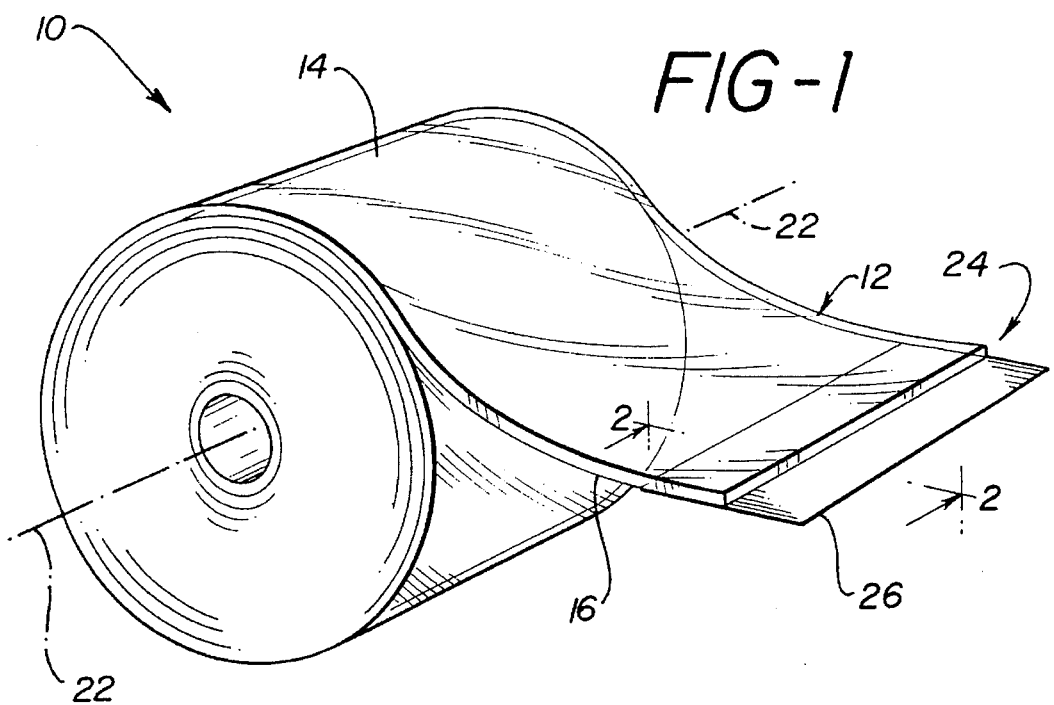
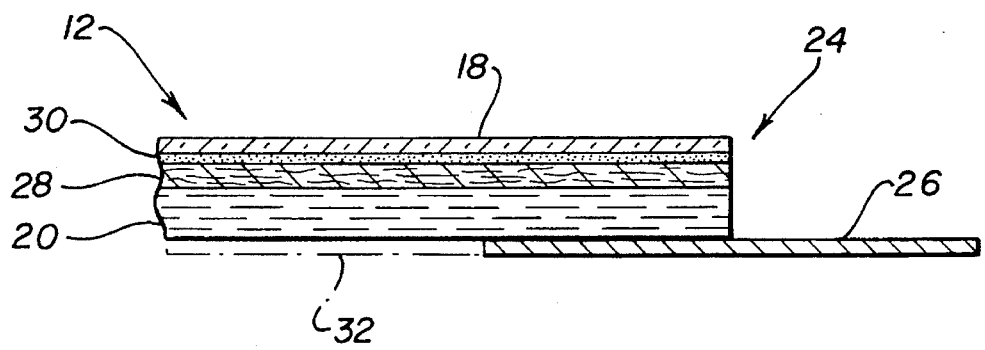

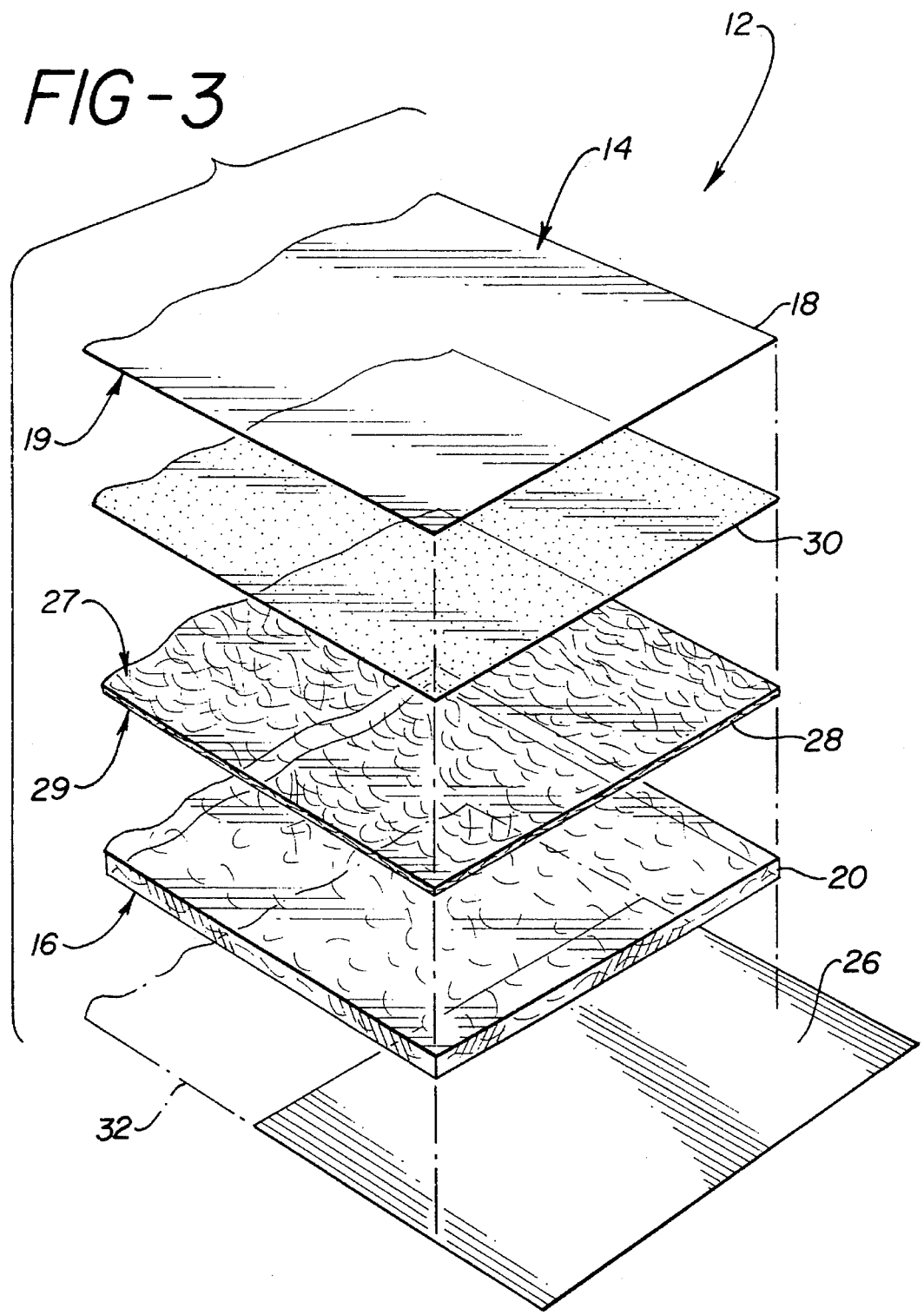

WOUND DRESSING HAVING A ROLL CONFIGURATION

CROSS-REFERENCE TO RELATED APPLICATION

This application is a continuation of U.S. application Ser. No. 07/741,318, filed Aug. 17, 1991, now abandoned.

BACKGROUND OF THE INVENTION

The present invention generally relates to wound dressings, and more particularly, to a wound dressing product having a roll configuration.

Secreting skin wounds, such as decubitus ulcers, burns and open surgical wounds, have long presented a medical challenge in keeping such wounds sterile and relatively dry. In that regard, burn wounds require a unique combination of therapy and dressing because the physiologic functions of the skin are absent or, at best, materially impaired. The accumulation of wound exudate, such as blood, pustulation, and other wound fluids, in the crevices of such wounds promotes growth of bacteria and crusted organisms which cause infection and delay the healing process. However, since it is often desirable to allow a wound to heal in a slightly "moist" or occlusive state which is believed to accelerate healing, excess wound exudate must be removed. If excess wound exudate remains on a wound, a "blister" of exudate can form under the wound dressing which is not only unsightly, but also may cause the wound dressing to leak, thereby defeating the aim of sterility. Existing methods of aspiration can lead to wound infection or can destroy sterility. Additionally, it is not desirable to remove all the wound exudate as that would result in a "dry" wound resulting in a slower healing process.

The art is replete with wound and/or surgical dressings for treating skin lesions, such as decubitus ulcers, open surgical wounds and burn wounds. For example, Mason, Jr. et al, U.S. Pat. No. 4,393,048, disclose a hydrogel wound treatment composition which dries to a powder after it is introduced into an open, draining wound to absorb wound exudate. However, dry hydrogel deteriorates as the wound fluids are absorbed resulting in lumping and uneven application. Additionally, such deteriorated lumps are difficult to remove from a wound site without damaging new cell tissue formed at the wound site. Furthermore, the progress of wound healing cannot be determined without removing, at least partially, the wound dressing from the wound site.

Aqueous moisture absorbing materials, such as a hydrogel material with a polyethylene glycol liquid curing agent as disclosed in Spence, U.S. Pat. No. 4,226,232, are easier to remove from the wound site, but cannot be sterilized by irradiation due to the formation of free radicals within the aqueous material. Another aqueous absorbing material used to absorb wound exudate is a hydrophilic polymer as disclosed in Rawlings et al, U.S. Pat. No. 4,657,006. Rawlings et al disclose a wound dressing which comprises a hydrophilic polymer having moisture and vapor permeability characteristics. However, a problem with the Rawlings et al wound dressing is that the wound exudate absorbed by the hydrophilic polymer hardens or solidifies the polymer, allowing pockets to develop between the polymer and the wound which provides an excellent environment for bacteria proliferation.

Yet another problem with the wound dressings known in the art is that they have been packaged and sold in finite strips or squares which may or may not be large enough to cover the wide range of wounds found on the patient. There are, however, bandages disposed in a generally roll form such that the bandage may be cut to the desired length and/or wrapped around, for example, the leg of a patient. Parker et al, U.S. Pat. No. 5,003,970 disclose a roll form medical bandage comprising an outer elongated sleeve formed of a moisture-impervious material and an elongated medical material. The elongated medical material includes a substrate comprised of layers of woven fabric and a tubular wrapping formed of a non-woven fiber. The substrate is impregnated or coated with a reactive system which remains stable when maintained in a moisture-free environment, but which hardens when exposed to sufficient moisture to form a rigid structure. Such a medical bandage is not conducive for healing wounds, such as burns, since it does not readily or continually absorb wound exudate as the wound heals. Rather, the bandage system hardens to a rigid structure when contacted with a wound emitting large amounts of wound exudate and other fluids, thereby preventing any further absorption of such fluids into the bandage. Moreover, air pockets are formed between the bandage and the wound which provides an excellent environment for bacteria proliferation. Therefore, it would be desirable to have a wound dressing which allows for easy dispensing and application and which has the ability to absorb large amounts of wound exudate, yet retain its original structure.

Frank, U.S. Pat. No. 5,006,401, discloses a roll pin extensible bandage having a hydrocolloidal adhesive composition laminated thereto. While Frank suggests that the hydrocolloidal adhesive is resistant to wound exudate fluids and can swell to absorb such fluids, hydrocolloidal adhesives, by their very nature, break apart into pieces after absorbing sufficient amounts of wound exudate. As a result, fragments and particulates of the hydrocolloidal adhesive are deposited in the wound, thereby inhibiting the healing process. Moreover, when the bandage, as disclosed by Frank, is removed from the wound, additional pieces and fragments of the hydrocolloidal adhesive adhere to the wound and the new cell tissue forming at the wound site. Consequently, it would be desirable to have a wound dressing which includes a dressing material which not only absorbs large amounts of wound exudate and other body fluids, but also maintains its structural integrity even after the removal of the wound dressing from the wound site. Additionally, it would be desirable to have such a dressing material which does not adhere to the new cell tissue of the wound.

Accordingly, there is a need for a wound dressing which facilitates dispensing and application of the wound dressing to a wide range of wounds which may be found on a patient's body. There is also a need for a wound dressing which includes a dressing material which has the ability to absorb large amounts of wound exudate and other body fluids, yet maintain its structural integrity even upon removal of the wound dressing from the wound.

SUMMARY OF THE INVENTION

The present invention meets the aforementioned needs by providing a wound dressing product in a roll configuration so as to facilitate dispensing and application of the wound dressing product to wounds found on a patient. The wound dressing product includes a wound dressing laminate wrapped into a roll such that the user can access a sufficient length of wound dressing laminate to cover wounds of varying sizes found on the patient's body.

In accordance with one aspect of the invention, the wound dressing product comprises a wound dressing laminate having a first side and a second side. The wound dressing laminate itself comprises a plurality of layers including a backing layer which forms the first side of the wound dressing laminate and a hydrogel layer which forms the second side of the wound dressing laminate. The roll configuration is formed by having the wound dressing laminate spirally wrapped about a center axis such that the wound dressing laminate terminates at a leading end and the first side of the wound dressing laminate forms the outer surface of the wound dressing product. Further, the hydrogel layer may be adhesively secured to the backing layer. The wound dressing product may include a cylindrical core positioned such that the center axis generally passes through the cylindrical core to provide additional support for the wound dressing product.

In accordance with another aspect of the invention, the wound dressing product comprises a wound dressing laminate having a plurality of layers including a backing layer made from a material which prevents the transmission of bacteria, also referred to herein as a bacterial barrier layer. The backing layer has a first side and a second side wherein the first side of the backing layer forms the first side of the wound dressing laminate. The wound dressing laminate further includes a bonding layer coated on the second side of the backing layer, a reticulated layer impregnated with a hydrogel material having a first and a second side wherein the first side of the reticulated layer is secured to the bonding layer, and a hydrogel layer comprising a hydrogel material overlying the second side of the reticulated layer. Further, the hydrogel layer forms the second side of the wound dressing laminate. As with the previous embodiment, the wound dressing laminate is spirally wrapped about a center axis such that the first side of the wound dressing laminate forms the outer surface of the wound dressing product.

In accordance with yet another aspect of the invention, the wound dressing product comprises a wound dressing laminate having a plurality of layers including a transparent bacterial barrier layer having a first side and a second side wherein the first side of the bacterial barrier layer forms the first side of the wound dressing laminate, and a transparent hydrogel layer overlying the second side of the backing layer which forms the second side of the wound dressing laminate. The wound dressing laminate is spirally wrapped about a center axis such that the first side of the wound dressing laminate forms the outer surface of the wound dressing product.

The wound dressing product may further comprise an open cell, scrim material layer impregnated with a hydrogel material which is interposed between the bacterial barrier layer and the hydrogel layer. The wound dressing product further includes a bonding layer for adhesively securing the scrim layer to the bacterial barrier layer. Additionally, a release liner may be releasably secured to the second side of the wound dressing laminate. All of the layers of the wound dressing laminate are transparent, thereby permitting visual inspection of the wound without removal of the wound dressing laminate. The transparent feature, therefore, minimizes the frequency of having to remove the wound dressing laminate.

Accordingly, it is a feature of the present invention to provide a wound dressing in a roll configuration so as to facilitate dispensing and application to a wide range of wounds having varying sizes; it is also a feature of the invention to provide a wound dressing in a roll configuration which includes a dressing material which has the ability to absorb large amounts of wound exudate, as well as other body fluids, yet maintain its structural integrity even upon removal of the wound dressing from the wound. Other features and advantages of the invention will be apparent from the following detailed description, the accompanying drawings and the appended claims.

BRIEF DESCRIPTION OF THE DRAWINGS

FIG. 1 is perspective view of the wound dressing product having a roll configuration;

FIG. 2 is a cross-sectional view of the wound dressing laminate of the wound dressing product taken along view line 2—2 in FIG. 1; and FIG. 3 is an exploded perspective view of the wound dressing laminate illustrated in FIG. 2.

DETAILED DESCRIPTION OF THE PREFERRED EMBODIMENT

The present invention is directed to a wound dressing product having a roll configuration which allows for easy and quick dispensing and application of a wound dressing laminate to a wide variety of wounds found on a patient. The wound dressing laminate of the invention is especially conducive for wounds including but not limited to burns and the like, as it is preferably comprised of a hydrogel material which readily absorbs wound exudate and other body fluids without breaking apart or adhering to the new cell tissue of a wound so as to expedite the healing process.

Referring now to FIG. 1, a perspective view of the wound dressing product 10 having a roll configuration is illustrated. The wound dressing product 10 comprises a wound dressing laminate 12 having a first side 14 and a second side 16. The wound dressing laminate 12 itself comprises a plurality of layers including, at a minimum, a backing layer 18 (best seen in FIGS. 2 and 3) which forms the first side 14 of the wound dressing laminate 12 and a hydrogel layer 20 (shown in FIGS. 2 and 3) which forms the second side 16 of the wound dressing laminate 12. The wound dressing laminate 12 is spirally wrapped about a center axis 22 such that the wound dressing laminate 12 terminates at a leading end 24 and the first side 14 of the wound dressing laminate 12 forms the outer surface of the wound dressing product 10. If the wound dressing laminate 12 only includes the backing layer 18 and the hydrogel layer 20, it is preferable to have the hydrogel layer 20 secured to the backing layer 18 by an adhesive or by any other means. The wound dressing product 10 may further comprise a cylindrical core positioned such that the center axis 22 generally passes through the cylindrical core. The cylindrical core may include any known structure known in the art. For example, a spool may be used as the cylindrical core which may further be attached to a stand for added stability when dispensing the wound dressing product 10 of the present invention.

As shown in FIG. 1, the leading end 24 of the wound dressing laminate 12 may further include a release liner strip 26 disposed on the second side 16 of the wound dressing laminate 12 to facilitate unwrapping of the wound dressing laminate 12. The unwrapping is facilitated in that the release liner strip 26 prevents the leading end 24 from adhering to the outer surface of the wound dressing product 10 which typically renders access to the leading end 24 difficult. Preferably, the release liner strip 26 is coated with a silicone polymer to facilitate further the unwrapping of the wound dressing laminate 12. By having the release liner strip 26 disposed on the second side 16, which preferably comprises the hydrogel layer 20, the leading end 24 does not adhere to the outer surface of the wound dressing product 10, but rather, remains free for easy access thereto.

In use, the user initially removes the wound dressing product 10 from any protective packaging and grasps the leading end 24 which is freely accessible by virtue of the release liner strip 26. The wound dressing product 10 is then unwrapped to a length sufficient for application to the wound and cut from the roll configuration. The unwrapping of the wound dressing product 10 is convenient since the preferred dressing material (described more fully below) comprising the hydrogel layer 20 possesses an optimal balance of adhesive properties which is strong enough to secure the wound dressing product 10 in a roll configuration yet allows for easy unwrapping. The release liner strip 26 can be removed from the leading end 24 and placed on the newly formed leading end created by the cutting away of the wound dressing laminate 12. This ensures that the leading end 24 remains freely accessible. Alternatively, the release liner strip 26 may be disposed since after a piece of the wound dressing laminate 12 is removed, the new leading end will, at least partially, remain accessible.

With reference to FIG. 2 and FIG. 3, FIG. 2 shows a cross-sectional view of the wound dressing laminate 12 taken along view line 2—2 in FIG. 1, while FIG. 3 illustrates an exploded view of the wound dressing laminate 12 shown in FIG. 2. The wound dressing laminate 12 may further include a reticulated layer 28 having a first side 27 and a second side 29 and which is impregnated with a hydrogel material. The backing layer 18 has a first side which forms the first side 14 of the wound dressing laminate 12. Also, as best seen in FIG. 3, the backing layer 18 has a second side 19 which faces a bonding layer 30. Preferably, the reticulated layer 28 is interposed between the backing layer 18 and the hydrogel layer 20 of the wound dressing laminate 12. The wound dressing laminate 12 may also include the aforementioned bonding layer 30 for adhesively securing the reticulated layer 28 to the backing layer 18. Those skilled in the art will appreciate that the reticulated layer 28 may be thermally secured to the backing layer 18 as well as adhesively secured thereto with the bonding layer 30. The bonding layer 30 may be formed of any adhesive material suitable for securing the reticulated layer 28 to the backing layer 18. For example, a medical grade acrylic adhesive of which many are commercially available, may be used in accordance with the invention.

With respect to the backing layer 18, it is preferable that backing layer 18 be formed of a material which prevents the transmission of bacteria. Accordingly, the backing layer 18 may also be referred to as a bacterial barrier layer. A multitude of materials may be used for this purpose including but not limited to polyurethane films. Thus, the backing layer 18 not only serves as a supporting member for the wound dressing product 10, but additionally, serves as a bacterial barrier layer for the wound itself. Those skilled in the art will appreciate that, in addition to preventing the transmission of bacteria, materials which also prevent the transmission of odors may be used as the material for the backing layer 18. It should be understood, however, that it is preferable that the backing layer 18 be oxygen and moisture permeable so as to promote and expedite the healing of the wound. The reticulated layer 28 may comprise any suitable reinforcing material, such as reticulated foam, scrim or a non-woven material. The materials, however, should be sufficiently absorbent to permit the hydrogel material to be impregnated therein.

The release liner strip 26 can be formed from any of a vast number of materials used for similar purposes. The release liner strip 26 may extend over the entire second side 16 of the wound dressing laminate 12, as shown by phantom line 32 in FIG. 2, without departing from the scope of the invention. A wound dressing product 10 which includes a release liner strip 26 over the entire second side 16 can be easier to unwrap by virtue of the non-adhesive qualities of the release liner strip 26. The user, however, must first remove the release liner strip 26 before affixing the wound dressing laminate 12 to the wound, thereby preventing quick application of the wound dressing laminate 12. Accordingly, the preferred wound dressing product 10 only includes the release liner strip 26 at the leading end 24 as described above.

The hydrogel layer 20 preferably comprises a hydrogel material having the ability to absorb wound exudate as well as other body fluids without losing its structural integrity. Moreover, the hydrogel material has sufficient adhesive characteristics to adhere to the wound without also adhering to the new cell tissue formed on the wound, especially when the wound dressing laminate 12 is removed from the wound site.

The preferred polyurethane hydrogel material is made from the following reactants: (a) from about 0% to about 90% by weight polyhydric alcohol; (b) from about 6% to about 60% by weight isophoronediisocyanate terminated prepolymer; (c) from about 4% to about 40% by weight polyethylene oxide based diamine; (d) up to about 2% by weight sodium chloride; and (e) the balance water. The polyhydric alcohol is preferably selected from the group consisting of polypropylene glycol, polyethylene glycol and glycerine. Most preferably, the polyurethane hydrogel material is made from the following reactants: (a) from about 15% to 30% by weight polypropylene glycol; (b) from about 8% to 14% by weight isophoronediisocyanate terminated prepolymer; (c) from about 5% to 10% by weight polyethylene oxide based diamine; (d) up to 1% by weight sodium chloride; and (e) the balance water. Most preferably, the polyurethane hydrogel material is made from the following reactants: (a) from about 16% to 17% by weight polypropylene glycol; (b) from about 10% to 12% by weight isophoronediisocyanate terminated prepolymer; (c) from about 7% to 9% by weight polyethylene oxide based diamine; (d) about 0.5% to 1% by weight sodium chloride; and (e) the balance water.

The isophoronediisocyanate terminated polymer is preferably based on polyols containing more than about 40% polyethylene oxide and having an isocyanate content of about 3% by weight. The molecular weight is preferably in a range from 1500–8000 and most preferably, from about 4000 to 5000. The molecular weight of the polyethylene oxide based diamine is preferably in a range from about 200 to 6000 and most preferably, about 2000. Those skilled in the art will appreciate that all of the constituents with the preferred hydrogel material may be readily synthesized or purchased commercially.

It should be appreciated that the aforementioned hydrogel compositions are for a stable hydrogel material in its final product form. The preferred hydrogel material possesses superior healing and absorbing properties and has a gel-like consistency which creates a bond between the wound dressing laminate 12 and the wound site without actually creating an actual adhesive attachment that would damage new cell tissue upon removal. The preferred hydrogel material readily absorbs wound exudate, as well as other body fluids, and permits the neat and clean removal of the wound dressing laminate 12 when it requires replacement.

The hydrogel material, which is impregnated in the reticulated layer 28, is preferably the same hydrogel material used to form the hydrogel layer 20 of the wound dressing laminate 12. Those skilled in the art should understand that other hydrogel material formulations other than those described above may be used without departing from the scope of the invention. For example, hydrogels having different constituents from the hydrogel material described above may be suitable for the wound dressing product 10 having a roll configuration. The preferred hydrogel material, however, allows the wound dressing laminate 12 to be wrapped into a roll configuration and yet, be easily unwrapped to the desired length by the user. The preferred hydrogel material also provides a bio-compatible, non-irritating, fluid absorbing, bacterial protective, cushioning media for application to the wound site. The hydrogel material is especially conducive for severe burns as well as for other types of wounds found on a patient.

Moreover, the preferred hydrogel material may be transparent, thereby permitting the inspection of the wound without removing the wound dressing laminate 12 from the patient provided that the other layers of the wound dressing laminate 12 are transparent, as well. The preferred wound dressing product 10, therefore, will have a wound dressing laminate 12, including the backing layer 18, the bonding layer 30, the reticulated layer 28 and the hydrogel layer 20, all of which are transparent, minimize the need for frequently removing the wound dressing laminate 12 from the wound.

Having described the invention in detail and by reference to preferred embodiments thereof, it will be apparent that modifications and variations are possible without departing from the scope of the invention which is defined in the appended claims. For example, a hydrogel material having a different composition from that of which is described herein may be used.

What is claimed is:

1. A wound dressing product, comprising:

a wound dressing laminate comprising a plurality of layers including a backing layer which forms said first side of said wound dressing laminate; and a polyurethane hydrogel layer which forms substantially all of the outer surface of said second side of said wound dressing laminate;

said wound dressing laminate being spirally wrapped about a center axis such that said wound dressing laminate terminates at a leading end and said first side of said wound dressing laminate forms the outer surface of said wound dressing product, said wound dressing laminate further comprising a reticulated layer being interposed between said backing layer and said hydrogel layer.

2. The wound dressing product of claim 1 wherein said wound dressing laminate further comprises a bonding layer for securing said reticulated layer to said backing layer.

3. A wound dressing product, comprising:

a wound dressing laminate having a first side and a second side, said wound dressing laminate comprising a backing layer made from a material which prevents the transmission of bacteria, said backing layer having a first side and a second side wherein said first side of said backing layer forms said first side of said wound dressing laminate;

a bonding layer coated on said second side of said backing layer;

a reticulated layer being sufficiently absorbent to be impregnated with a polyurethane hydrogel material having a first and a second side, said first side of said reticulated layer being secured to said bonding layer, said reticulated layer being selected from the group consisting of foams, scrim, and non-woven materials; and a polyurethane hydrogel layer comprising said hydrogel material overlying said second side of said reticulated layer, said hydrogel layer forms substantially all of the outer surface of said second side of said wound dressing laminate;

said wound dressing laminate being spirally wrapped about a center axis such that said first side of said wound dressing laminate forms the outer surface of said wound dressing product.

4. The wound dressing product of claim 3 wherein said hydrogel material is made from the following reactants:

(a) from about 0% to about 90% by weight polyhydric alcohol;

(b) from about 6% to about 60% by weight isophoronediisocyanate terminated prepolymer;

(c) from about 4% to about 40% by weight polyethylene oxide based diamine;

(d) up to about 2% by weight sodium chloride; and (e) the balance water.

5. A wound dressing product comprising:

a wound dressing laminate having a first side and a second side, said wound dressing laminate comprising a plurality of layers including a transparent bacterial barrier layer having a first side and a second side, said first side of said bacterial barrier layer forms said first side of said wound dressing laminate; and a transparent polyurethane hydrogel layer coextensively overlying said second side of said bacterial barrier layer which forms substantially all of the outer surface of said second side of said wound dressing laminate;

a scrim layer impregnated with a transparent hydrogel material, said scrim layer being interposed between said bacterial barrier layer and said hydrogel layer;

said wound dressing laminate being spirally wrapped about a center axis such that said first side of said wound dressing laminate forms the outer surface of said wound dressing product.

6. The wound dressing product of claim 5 further comprising a cylindrical core positioned such that said center axis passes through said cylindrical core.

7. The wound dressing product of claim 5 wherein said wound dressing laminate further includes a transparent bonding layer for securing said scrim layer to said bacterial barrier layer.

8. The wound dressing product of claim 5 wherein said bacterial barrier layer is made from a polyurethane material.

9. The wound dressing product of claim 5 wherein said polyurethane hydrogel layer is formed from the following reactants:

(a) from about 0% to about 90% by weight polyhydric alcohol;

(b) from about 6% to about 60% by weight isophoronediisocyanate terminated prepolymer;

(c) from about 4% to about 40% by weight polyethylene oxide based diamine;

(d) up to about 2% by weight sodium chloride; and (e) the balance water.

10. The wound dressing product of claim 5 further comprising a release liner releasably secured to said second side of said wound dressing laminate.

11. A wound dressing product comprising:
   a wound dressing laminate having a first side and a second side, said wound dressing laminate comprising a plurality of layers including
      a transparent bacterial barrier layer having a first side and a second side, wherein said first side of said bacterial barrier layer forms said first side of said wound dressing laminate;
      a transparent bonding layer coated on said second side of said backing layer;
      a scrim layer impregnated with a transparent polyurethane hydrogel material having a first and a second side, said first side of said scrim layer being secured to said bonding layer; and
      a transparent polyurethane hydrogel layer made from said hydrogel material coextensively overlying said second side of said scrim layer, said hydrogel layer forms substantially all of the outer surface of said second side of said wound dressing laminate;
   a release liner releasably secured to said hydrogel layer;
      said wound dressing laminate being spirally wrapped about a center axis such that said first side of said wound dressing laminate forms the outer surface of said wound dressing product.

12. The wound dressing product of claim 11 wherein said polyurethane hydrogel material is formed from the following reactants:
   (a) from about 0% to about 90% by weight polyhydric alcohol;
   (b) from about 6% to about 60% by weight isophorone-diisocyanate terminated prepolymer;
   (c) from about 4% to about 40% by weight polyethylene oxide based diamine;
   (d) up to about 2% by weight sodium chloride; and
   (e) the balance water.

* * * * *